(12) United States Patent  (10) Patent No.: US 8,623,281 B2
Setayesh et al.  (45) Date of Patent: Jan. 7, 2014

(54) ELECTRONIC SENSOR FOR NITRIC OXIDE

(75) Inventors: Sepas Setayesh, Eindhoven (NL);
Nicolaas Petrus Willard, Eindhoven (NL); Dagobert Michel De Leeuw, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 12 days.

(21) Appl. No.: 13/139,582

(22) PCT Filed: Dec. 10, 2009

(86) PCT No.: PCT/IB2009/055637
§ 371 (c)(1),
(2), (4) Date: Jun. 14, 2011

(87) PCT Pub. No.: WO2010/070544
PCT Pub. Date: Jun. 24, 2010

(65) Prior Publication Data
US 2011/0239735 A1  Oct. 6, 2011

(30) Foreign Application Priority Data

Dec. 16, 2008 (EP) .................................... 08171816

(51) Int. Cl.
*G01N 27/00* (2006.01)
(52) U.S. Cl.
USPC ....................................................... 422/82.01
(58) Field of Classification Search
USPC ....................................................... 422/82.01
See application file for complete search history.

(56) References Cited

U.S. PATENT DOCUMENTS

| 5,079,595 A | 1/1992 | Suzuki et al. |
| 5,431,883 A * | 7/1995 | Barraud ................... 422/82.01 |
| 5,603,820 A | 2/1997 | Malinski et al. |
| 2002/0167003 A1 | 11/2002 | Campbell et al. |
| 2004/0072360 A1* | 4/2004 | Naaman et al. ............... 436/116 |
| 2007/0048180 A1 | 3/2007 | Gabriel et al. |
| 2007/0281362 A1 | 12/2007 | Vink et al. |
| 2009/0054798 A1* | 2/2009 | Varney et al. .................. 600/532 |

FOREIGN PATENT DOCUMENTS

| WO | 02057738 A2 | 7/2002 |
| WO | 02088691 A2 | 11/2002 |
| WO | 2007010425 A1 | 1/2007 |
| WO | 2007138506 A1 | 12/2007 |

OTHER PUBLICATIONS

Barker et al: "A Hybrid Phthalocyanine/Silicon Field-Effect Transistor Sensor for NO2"; Thin Soled Films 284-285 (1996), pp. 94-97.
Smits, E.C.P.: "Bottom-Up Organic Integrated Circuits"; Nature, 2008, Vol. 455, pp. 956-959.

* cited by examiner

*Primary Examiner* — Monique Cole

(57) ABSTRACT

Disclosed is a semiconductor device (1) for determining NO concentrations in fluids such as exhaled breath. The device (1) typically comprises a pair of electrodes (18) separated from each other to define a channel region (16) in an organic semiconductor (14), a gate structure (10) for controlling said channel region, and a receptor layer (22) at least partially overlapping said channel region, said receptor layer comprising a porphine or phtalocyanine coordination complex including a group III-XII transition metal ion or a lead (Pb) ion for complexing NO. Such a semiconductor device is capable of sensing NO concentrations in the ppb range.

15 Claims, 4 Drawing Sheets

ELECTRONIC SENSOR FOR NITRIC OXIDE

FIELD OF THE INVENTION

The present invention relates to a semiconductor device comprising a pair of electrodes separated from each other to define a channel region in an organic semiconductor layer, a gate structure for controlling said channel region, and a receptor layer at least partially overlapping said channel region.

The present invention further relates to a sensing device comprising such a semiconductor device.

The present invention yet further relates to a method of determining a nitric oxide concentration in exhaled breath with a breath analyzer.

BACKGROUND OF THE INVENTION

In the field of medical care, there exist many devices to aid physicians and patients in monitoring a wide range of analyte concentrations related to the patient's body. Such concentrations can for instance be used to monitor if a medical condition is properly controlled by administered drugs, or to aid in reaching a diagnosis of a medical condition from which the patient may be suffering.

Examples of such devices include sensor devices that may be brought into contact with a bodily fluid such as blood or urine, and sensor devices that determine the concentration of a chemical agent in breath expelled by a monitored subject. The sensing functionality of such devices may be provided by dedicated semiconductor devices such as a chemically modified field effect transistor (ChemFET), in which the current characteristics of the transistor are correlated to the concentration of a target analyte.

Well-known examples of such semiconductor devices include transistors covered by a selective membrane such that the transistor would only be exposed to analytes capable of passing the membrane barrier. However, such devices can require complex manufacturing processes, which make them costly.

Some analytes occur in the monitored medium in minute concentrations only, such that accurate detection of these analytes is quite challenging. An example of such an analyte is nitric oxide (NO), which can occur in exhaled breath of human patients and is, amongst others, an indicator of the presence of an inflammation in the lungs of the patient. For this reason, breath analyzers capable of accurately determining the NO concentration in expelled breath are important tools in the treatment of respiratory diseases such as asthma.

US patent application US 2007/0048180 discloses a breath analyzer comprising a nanoelectric sensor capable of determining NO concentrations in the parts-per-million (ppm) range. The nanoelectric sensor comprises a substrate over which one or more nanostructures are disposed. The nanostructures are electrically connected to one or more conducting elements and a recognition material is operatively associated with the nanostructures for interacting with analytes of interest. This document teaches that examples of such a recognition material include metal complexes of porphyrins and phthalocyanins, as well as conductive polymers such as polyaniline and polypyrrole.

A drawback of this breath analyzer is that the sensitivity of the nanoelectric sensor to NO does not extend to the parts-per-billion (ppb) range, which is the typical concentration range of NO in human breath. Consequently, the usefulness of this breath analyzer for the purpose of detecting NO in exhaled human breath is limited. In addition, the use of nanostructures as channel material means that standard manufacturing processes for manufacturing semiconductor devices cannot be used, which adds to the cost of both the nanoelectric sensor and the breath analyzer.

SUMMARY OF THE INVENTION

The present invention seeks to provide a semiconductor device capable of sensing NO concentrations in the ppb range.

The present invention further seeks to provide a sensing device comprising such a semiconductor device.

The present invention yet further seeks to provide a method of determining a NO concentration in exhaled breath.

In accordance with a first aspect of the present invention, there is provided a semiconductor device comprising a pair of electrodes separated from each other to define a channel region in an organic semiconductor layer, and a gate structure for controlling said channel region, said device further comprising a receptor layer at least partially overlapping said channel region, said receptor layer comprising a nitric oxide coordination complex selected from Formula I or Formula II:

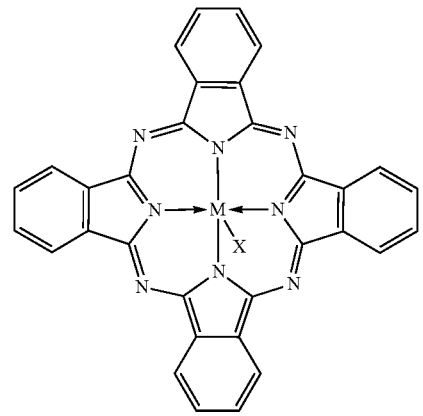

Formula I

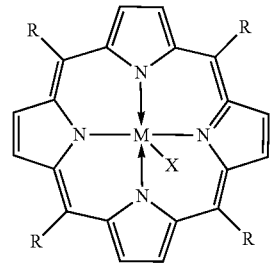

Formula II wherein M is Pb or a transition metal ion selected from group 3 to group 12 transition metals, and wherein X is a nitrate or a halide ion.

It has been surprisingly found that such a semiconductor device, e.g. a field-effect transistor is sensitive to NO concentrations in the ppb range. Although it is not yet fully understood what the mechanism for this unexpected sensitivity is, it is believed that the predominantly planar shape of these coordination complexes results in a layer in which the overall dipole moment of the layer, at least in the direction perpendicular to the flow of charge carriers through the channel, is very small, such that when NO is coordinated to an axial position of the central metal atom of the coordination complex, the substantial change in the out-of-plane dipole moment of the coordination complex is sensed in the channel of the semiconductor device, thus influencing the conductive characteristics of the semiconductor device.

Any transition metal capable of coordinating NO may be used. Since it is believed that it is the out-of-plane NO dipole moment that is responsible for the change in the conductive characteristics of the semiconductor device, the type of transition metal is not crucial to the present invention. However, the transition metal ion is preferably selected from Sc, Ti, V, Cr, Mn, Fe, Co, Ni, Cu, Pb and Zn, because the ions of those metals are known to have good affinity for complexing NO. More preferably, the transition metal ion is a Fe ion because of its excellent affinity for coordinating with NO.

In a preferred embodiment, the nitric oxide coordination complex is the compound of Formula II, with R=phenyl and M=$Fe^{3+}$, i.e. iron (III) mesotetraphenylporphine. It has been demonstrated that the inclusion of this compound yields a semiconductor device that is particularly sensitive to changes in the NO concentration.

At this point, it is emphasized that the exact arrangement of the semiconductor device is not crucial to the present invention. For instance, the gate structure and the receptor layer may be located on opposite sides of the channel region, as for instance is the case in a bottom gate device in which the gate also acts as the carrier or substrate. The receptor layer may be in physical contact with the channel region, or may be separated from the channel region by a protective layer. The latter arrangement has the advantage that the channel region is protected from exposure to harmful agents, e.g. oxygen and water during its use, thus extending the lifetime of the device.

In an alternative embodiment, the receptor layer is arranged over the gate structure, such that the gate potential sensed by the channel region is modified by the out-of-plane dipole moment of the coordinated NO.

The semiconductor device may be a layered device, wherein the channel region forms part of an organic semiconductor layer, said layer further covering the electrode pair. This has the advantage that the semiconductor device may be formed using inexpensive manufacturing techniques such as spin-coating.

In an embodiment, the organic semiconductor channel region is a self-assembled monolayer, with the nitric oxide coordination complex being chemically bound to the monolayer. Consequently, the self-assembled monolayer comprises two regions; a first region acting as channel region and a second region acting as receptor region. This has the advantage that these regions may be formed in a single step. The chemical bond may comprise any suitable bond such as a covalent bond, an ionic bond, a Van der Waals bond, and a coordinative bond.

According to a further aspect of the invention, there is provided a sensing device such as a breath analyzer comprising a measuring chamber in communication with a fluid inlet, said measuring chamber comprising a semiconductor device of the present invention, a processor coupled to the semiconductor device for correlating a signal from the semiconductor device to a nitric oxide concentration; and an output for providing a user with the nitric oxide concentration. The output may for instance comprise a display. Such a sensing device is capable of determining a NO concentration in a fluid such as exhaled breath in the ppb range.

According to yet a further aspect of the present invention, there is provided a method of determining a nitric oxide concentration in exhaled breath, said method comprising providing the breath analyzer of the present invention, exhaling the breath into the inlet of the breath analyzer and determining the NO concentration.

BRIEF DESCRIPTION OF THE DRAWINGS

Embodiments of the invention are described in more detail and by way of non-limiting examples with reference to the accompanying drawings, wherein FIG. 1 schematically depicts a semiconductor device according to an embodiment of the present invention.

DETAILED DESCRIPTION OF THE EMBODIMENTS

Figure 1:
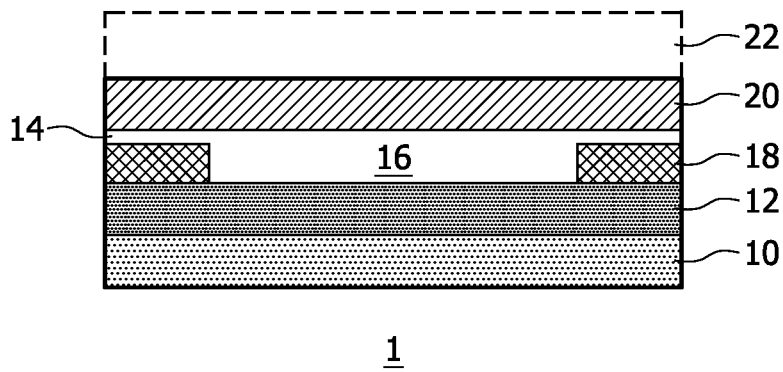

It should be understood that the Figures are merely schematic and are not drawn to scale. It should also be understood that the same reference numerals are used throughout the Figures to indicate the same or similar parts.

As will have become apparent, the inventive concept described in this application is the selection of appropriate receptor compounds that bring the sensitivity of a semiconductor device such as a FET for sensing NO concentrations into the ppb sensitivity range. It is foreseen that no specific embodiment of the semiconductor device is required to achieve such sensitivity, such that different implementations of such a semiconductor device may be used without departing from the scope of the present invention.

FIG. 1 shows an example implementation of a semiconductor device 1 in accordance with an embodiment of the present invention. The semiconductor device 1 shown in FIG. 1 is a dual-gate FET as previously described in PCT patent application WO 2007/138506, which is hereby incorporated by reference for the sake of brevity. The semiconductor device 1 comprises a gate electrode layer 10, a gate dielectric layer 12, and an organic semiconductor layer 14 including a channel region 16 in between two electrodes 18 that serve as source and drain terminals respectively. In FIG. 1, the organic semiconductor layer 14 is shown to cover the electrodes 18 by way of non-limiting example only. Other arrangements, such as an arrangement where the electrodes 18 are placed on the semiconductor layer 14 or an arrangement in which the organic semiconductor layer 14 is planarized to the level of the electrodes 18, are equally feasible.

The semiconductor device 1 further comprises a second dielectric layer 20 which may act as a protective layer for the channel region 16 and a receptor layer 22 comprising a coordination complex according to Formula I or II:

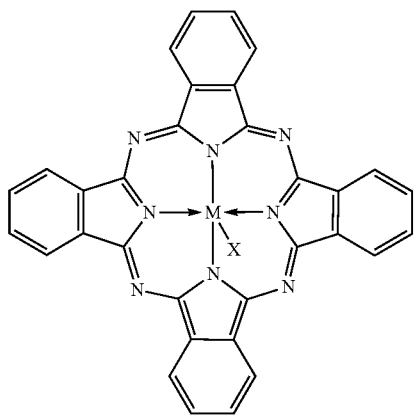

Formula I

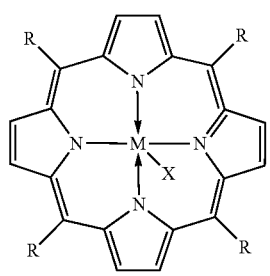

Formula II wherein M is a transition metal ion selected from group 3 to group 12 transition metals, wherein R is an unsubstituted or substituted arylene or heteroarylene functional group and wherein X is a nitride or a halide ion. Preferably, ions from the row IV transition metals Sc, Ti, V, Cr, Mn, Fe, Co, Ni, Cu, Pb and Zn are used because these ions are known to form good complexes with the phthalocyanins and porphins More preferably, Fe ions are used because these ions form especially stable complexes with these coordination compounds.

It has been found that the combination of the planarity and symmetry of such coordination complexes, e.g. the phthalocyanine complex of Formula I and the porphine complex of Formula II allow for the formation of an ordered receptor layer 22. It is believed that this ordering is important because it causes the overall dipole moment of the receptor layer 22 to be small, such that complexation of NO, which is believed to complex in an axial, i.e. out-of-plane, position on the metallic center of the complex, causes a substantial change in the overall dipole moment of the receptor layer 22.

At this point, it is mentioned that although Formulae 1 and 2 do not explicitly show substituents on the outer periphery of the porphine and phthalocyanine structures, it should be understood that non-hydrogen substituents may be present as long as the overall in-plane dipole moment is not substantially affected. Preferably, if such substituents are present, the compound according to Formula 1 or 2 should maintain some symmetry (i.e. should not belong to the $C_1$ point group).

The corresponding change in the electric field extends to the channel region 16, thus influencing its conductivity. This is why the FET shown in FIG. 1 is sometimes referred to as a dual-gate FET because both gate electrode layer 10 as well as the protective dielectric layer 20 together with the receptor layer 22 controls the channel current, with the protective dielectric layer 20 together with the receptor layer 22 acting as a floating gate.

The various other layers of the FET in FIG. 1 may be formed using materials as disclosed in WO 2007/138506. For instance, the gate electrode layer 10 may comprise any suitable conductive material such as heavily doped silicon or poly-Si, which may be salicided, a metal such as Ag, Cu, Al and/or Ni or organic materials such as PSS/PEDOT or polyaniline.

The gate dielectric layer 12 may comprise any suitable dielectric material such as amorphous metal oxides such as $Al_2O_3$, $Ta_2O_5$, transition metal oxides such as $HfO_2$, $ZrO_2$, $TiO_2$, $BaTiO_3$, $Ba_xSr_{1-x}TiO_3$, $Pb(Zr_xTi_{1-x})O_3$, $SrTiO_3$, $BaZrO_3$, $PbTiO_3$, $LiTaO_3$, rare earth oxides such as $Pr_2O3$, $Gd_2O_3$, $Y_2O_3$ or silicon compounds such as $Si_3N_4$, $SiO_2$ or microporous layers of SiO and SiOC. Furthermore, the first dielectric layer can comprise insulating polymers such as SU-8, BCB or PTFE.

The source and drain electrodes 18 can be fabricated using metals such as aluminium, gold, silver or copper or, alternatively, using conducting organic or inorganic materials. The organic semiconductor layer 16 can comprise materials selected from polyacetylenes, polypyrroles, polyanilines, polyarylamines, polyfluorenes, polynaphthalenes, polypphenylene sulfides or poly-p-phenylene vinylenes. The semiconductor layer also may be n-doped or p-doped to enhance conductivity.

The protective layer 20, which typically also is a dielectric layer, can be selected from the same materials as discussed for the gate dielectric layer 12. As the second dielectric layer also shields the layers below from outside conditions, waterproof coatings such as PVDF, PTFE, Zeonex™ or silicones may also be taken into consideration. Combinations of such materials are also feasible. For instance, in an embodiment, the protective layer 20 comprises a PVDF/PTFE co-polymer. The thickness of the gate dielectric layer 12 and the protective layer 20 is chosen such that leakage currents through these layers are controlled such that the sensitivity of the FET remains sufficient to detect NO concentrations in the ppb range. Suitable thicknesses typically depend on the combinations of the chosen materials. The skilled person will be able to determine the suitable thicknesses as a matter of routine skill during the design implementation of the semiconductor device 1.

Preferably, during operation of the field-effect transistor the capacitance of the assembly comprising the gate electrode layer 10 and the gate dielectric layer 12 is lower than the capacitance of the assembly formed by the protective layer 20 and the receptor layer 22. It has been found that the sensitivity of the field-effect transistor can be advantageously influenced by this capacitance relation, as has been explained in more detail in WO 2007/138506. However, it is expected that semiconductor devices for which this capacitance relationship does not hold, are still sensitive enough to detect NO concentrations in the ppb range.

The receptor layer 22 may be formed over the channel region 16, e.g. on the protective layer 20 in any suitable way. For instance, the coordination complex of Formula I or II may comprise a reactive group in the periphery of the ring structure to anchor the coordination complex onto a surface over the channel region 16. Such a reaction may for instance form a covalent, coordinative or ionic bond between the coordination complex and the receiving surface.

Alternatively, the coordination complex may be spin-coated onto the receiving surface. To this end, a suspension of the coordination complex in an organic solvent may be formed. This suspension may be activated using ultrasound to saturate the organic solvent with the coordination complex, after which the suspension may be filtered, with the filtrate being spin-coated onto the receiving surface. The coordination complex may be poorly soluble in the organic solvent, and the organic solvent should be reasonably volatile to allow for relatively quick evaporation of the solvent upon spin-coating to limit the duration of the semiconductor device manufacturing process. A non-limiting example of a suitable solvent is isopropylalcohol.

As a further alternative, a self-assembled monolayer of the coordination complex may be formed over the channel region 16. Other alternatives will be apparent to the skilled person.

In a preferred embodiment, the coordination complex is the compound in accordance to Formula III:

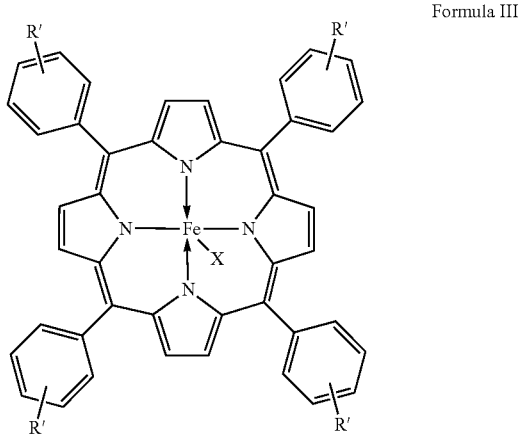

Formula III wherein R' may be hydrogen or one or more alkyl moiety such as a $C_1$-$C_{12}$ linear or branched alkyl moiety, as long as the overall (in-plane) dipole moment of the coordination complex remains small. Preferably, the coordination complex is a symmetrical complex for this reason. Also, X preferably is a halide such as $Cl^-$ but may also be another suitable ion such as a $NO_3^-$ ion. It has been found that a semiconductor device 1 containing a receptor layer 22 including this complex is particularly sensitive to NO.

This is demonstrated by the following example.

EXAMPLE I

A semiconductor device of FIG. 1 is formed as substantially described in WO 2007/138506. A $n^{++}$ doped poly-Si gate layer 10 is covered by a $SiO_2$ gate dielectric layer 12, onto which two gold electrodes 18 are formed. A polyarylamine semiconductor layer 14 is spin-coated over the $SiO_2$ layer 12 and the gold electrodes 18, thereby forming a channel region 16 between the gold electrodes 18. A protective PVDF/PTFE co-polymer layer 20 is deposited over the polyarylamine semiconductor layer 14, after which a receptor layer 22 is formed by spin-coating a solution of the coordination complex of Formula III with R'=H and X=$Cl^-$ in isopropylalcohol over the protective layer 20.

COMPARATIVE EXAMPLE I

A semiconductor device is formed as in example I without the formation of the receptor layer 22 over the protective PVDF/PTFE layer 20.

Figure 2:
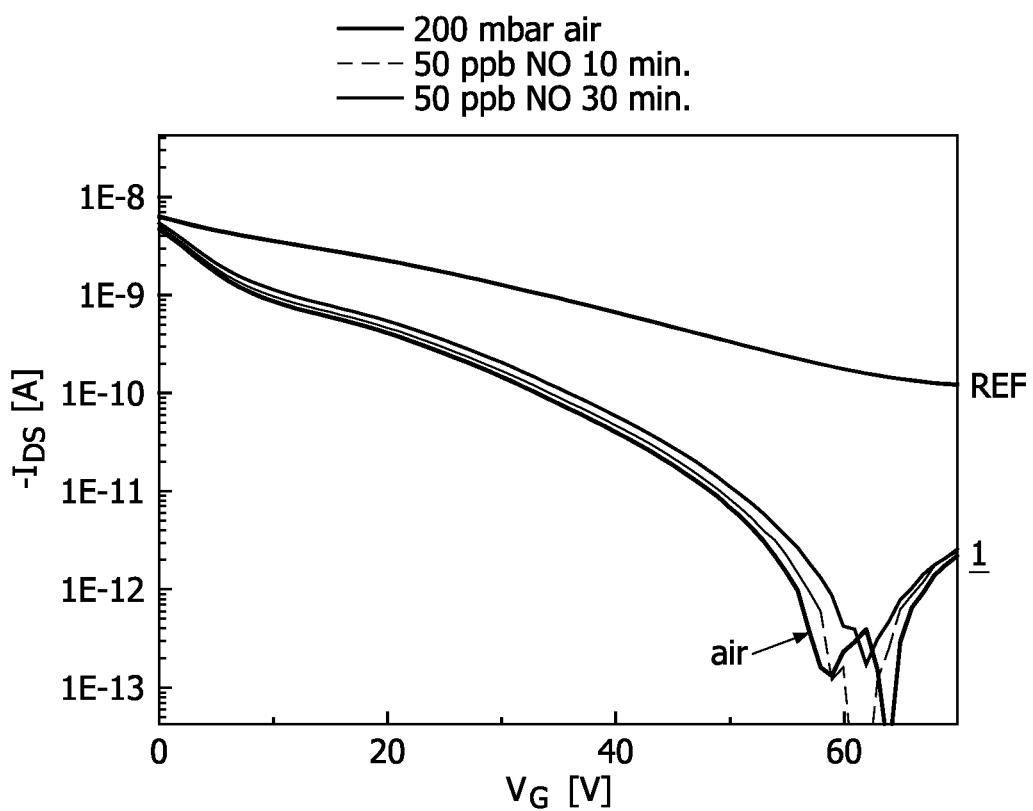
FIG. 2 schematically depicts the sensitivity of the semiconductor device of FIG. 1 to NO.

FIG. 2 shows the results of measurements performed with the semiconductor device of example I (labeled 1) and comparative example I (labeled REF). Both devices were exposed to an air flow comprising 50 ppb NO for 10 minutes and 30 minutes respectively at varying gate voltages $V_G$. In addition, the semiconductor device of example I of example 1 was exposed to a 200 mbar air flow as a further reference.

FIG. 2 clearly demonstrates the increased sensitivity of the semiconductor device 1 to NO compared to the reference device, as expressed by the change in current through the semiconductor device of the present invention. In addition, it is demonstrated that the semiconductor device of the present invention is capable of distinguishing between the blank reference, i.e. the 200 mbar air flow, and an air flow containing 50 ppb NO. Even after exposure to 50 ppb NO for just 10 minutes, the semiconductor device of example I is capable of distinguishing between the blank reference and an air flow comprising 50 ppb NO, especially close to the breakdown voltage of the device, i.e. between $V_G$=50-60 V. It should further be appreciated that although the differences in drain-source current between the blank reference and the air flow containing 50 ppb NO for gate voltages less than 50V appear modest, these differences are in fact measurable and reproducible, such that more modest gate voltages may be applied to detect NO in the ppb range in an air flow such as exhaled breath.

As can be seen from FIG. 2, the receptor layer 22 is still capable of sufficiently biasing the channel region 16 even though it is separated from the channel region 16 by the protective layer 20. For this reason, it is expected that other semiconductor device designs, e.g. transistor designs, in which the channel region 16 is separated from the receptor layer 22 are also feasible.

Figure 3:
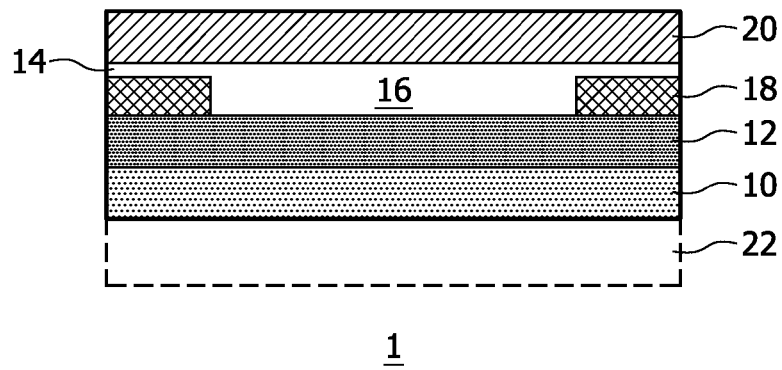
FIG. 3 schematically depicts a semiconductor device according to another embodiment of the present invention.

FIG. 3 is an example of such a design, in which the receptor layer 22 is provided over the gate electrode 10. This effectively turns the gate electrode 10 into a floating gate because the gate potential becomes the sum of the control voltage applied to the gate electrode and the electric field generated by the out-of-plane dipole moments of the NO molecules coordinated to the coordination complexes of the receptor layer 22.

Figure 4:
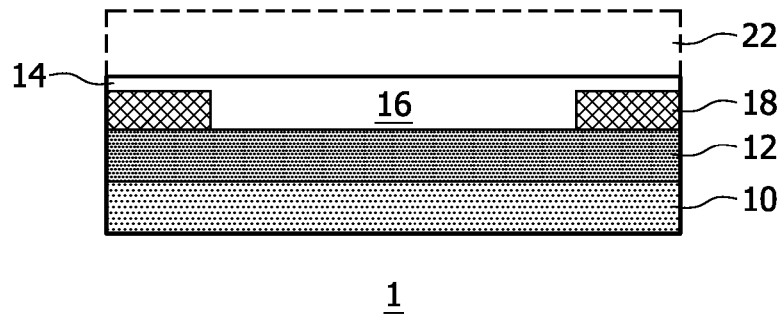
FIG. 4 schematically depicts a semiconductor device according to yet another embodiment of the present invention.

In an alternative embodiment, the receptor layer 22 may be applied directly over the organic semiconductor layer 14. This is shown in FIG. 4. It is expected that this semiconductor device has an even higher sensitivity to NO because of the closer proximity of the channel region 16 to the receptor layer 22.

Figure 5:
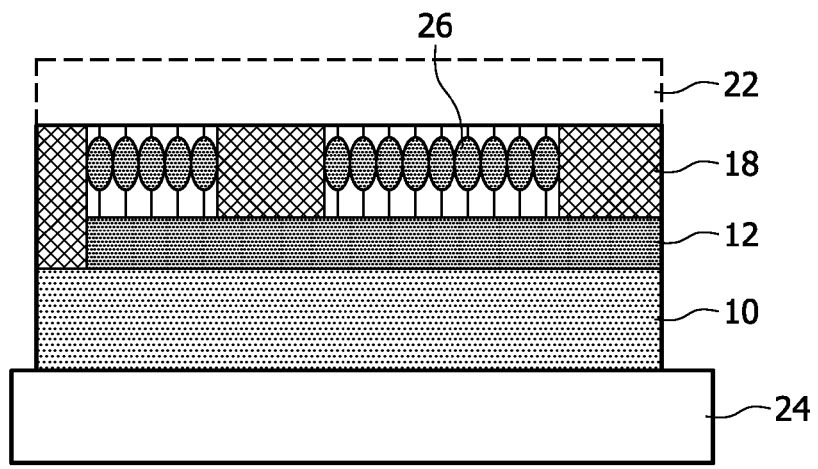
FIG. 5 schematically depicts a semiconductor device according to a further embodiment of the present invention in which the channel region comprises a self-assembled monolayer.

This is demonstrated by a further embodiment shown in FIG. 5, in which an organic semiconductor channel region 26 is formed by means of a self-assembled monolayer on the gate dielectric layer 12 in between the source and drain electrodes 18. The gate electrode layer 10 is formed on a substrate 24, which may be any suitable substrate such as a glass substrate or a silicon substrate. The receptor layer 22 is formed directly over the self-assembled monolayer 26 and the source/drain electrodes 18. An example of how to manufacture such a device is given in Example II. A discussion on materials suitable for use as self-assembled semiconducting materials in a semiconductor device as shown in FIG. 5 can be found in the article "Bottom-up organic integrated circuits" by E. C. P. Smits et al. in Nature, Vol. 455, 2008, pages 956-959.

EXAMPLE II

Figure 6:
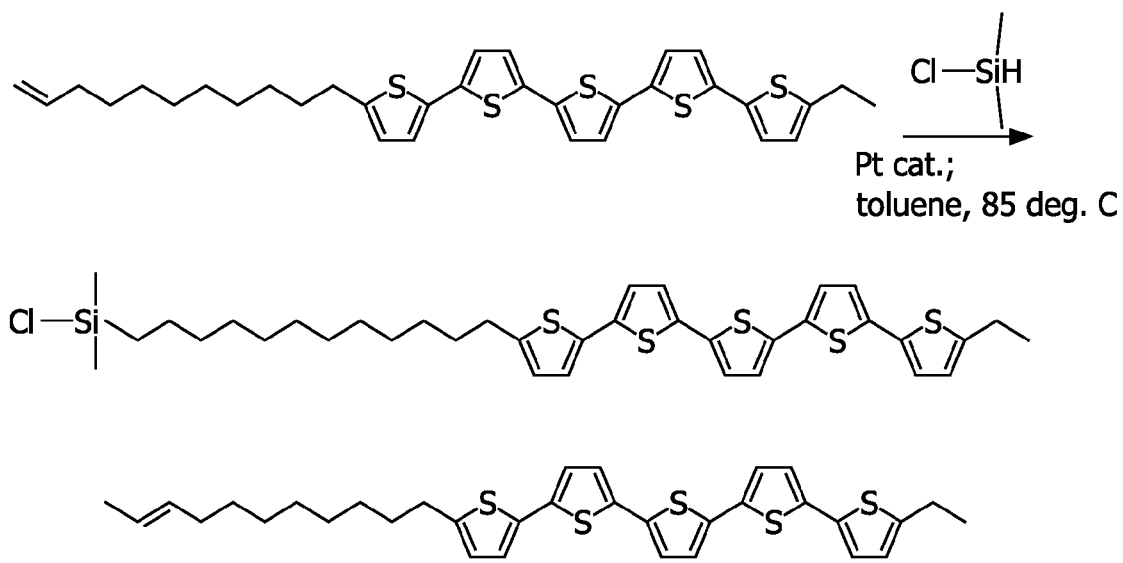
FIG. 6 depicts a reaction schedule for forming a compound suitable for self-assembly.

The active molecule 1 (see FIG. 6), chloro[11-(5''''-ethyl-2,2':5',2'':5''',2''''-quinquethien-5-yl)undecyl]dimethylsilane, was synthesized by hydrosilylation of 5-ethyl-5''''-undec-10-en-1-yl-2,2':5',2'':5''',2''''-quinquethiophene[1] (compound 2) with dimethylchlorosilane. About 50% of a by-product 5-ethyl-5''''-undec-9-en-1-yl-2,2':5',2'':5''',2''''-quinquethiophene (compound 3) having a migrated double bond compared to compound 1 was also formed. It proved impossible to separate compounds 1 and 3 by any conventional method. However, since compound 3 is a non-functional impurity i.e. it cannot covalently bind to a Si—OH surface, this product mixture could be used for preparation of the SAMFET as described in the aforementioned Nature publication. A receptor layer 22 is formed over the SAMFET by spin-coating a solution of the coordination complex of Formula III with R'=H and X=Cl⁻ in isopropylalcohol over the self-assembled monolayer.

Figure 7:
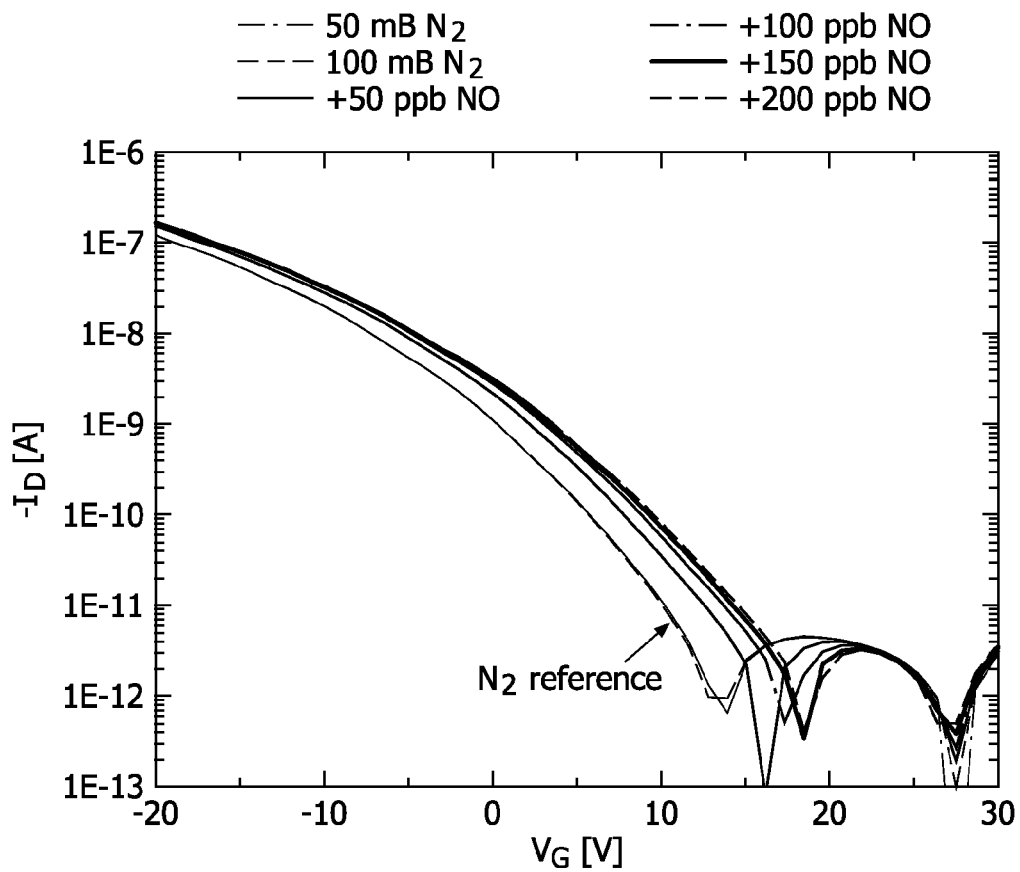
FIG. 7 schematically depicts the response of the semiconductor device of FIG. 5 to various NO concentrations.

FIG. 7 shows the results of measurements performed with the SAMFET semiconductor device of example II. The SAMFET semiconductor device of example II were exposed to an air flow comprising 50, 100, 150 and 200 ppb NO for 30 minutes at varying gate voltages $V_G$. In addition, the semiconductor device of example I of example 1 was exposed to a 50 mbar $N_2$ flow as a further reference. It is clearly demonstrated that a significant shift in on-current is achieved when the device is exposed to NO instead of $N_2$. In addition, the different NO concentrations lead to detectable differences in the on-current, in particular in the $V_G$=10V region.

Figure 8:
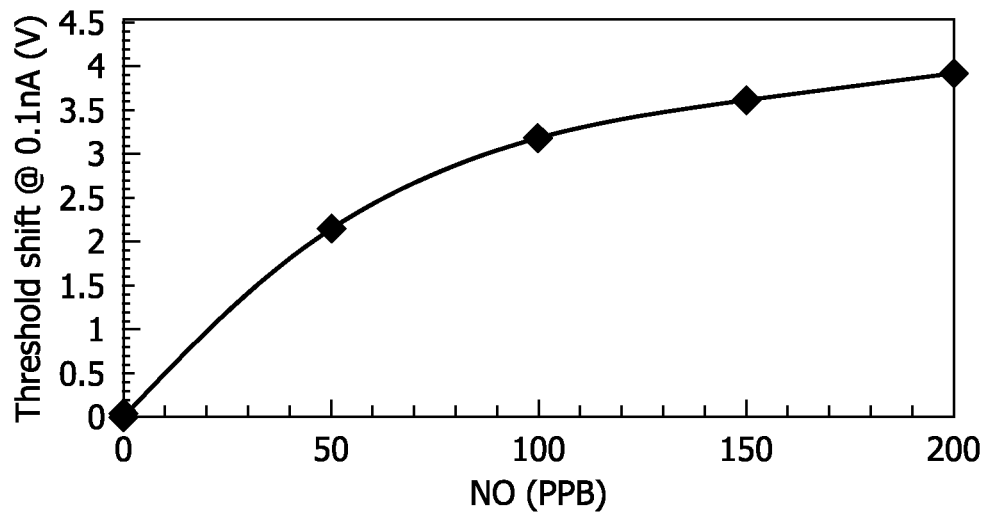
FIG. 8 schematically depicts the sensitivity of the semiconductor device of FIG. 5 to NO.

FIG. 8 shows the shift in the threshold voltage of the SAMFET semiconductor device of example II at a channel current of 0.1 nA as a function of the NO concentration in an air flow to which the transistor has been exposed. This clearly demonstrates that NO concentrations as little as 20-30 ppb cause a threshold voltage shift in the region of 1V, which may be detected by a suitable detection device such as a signal processor.

Figure 9:
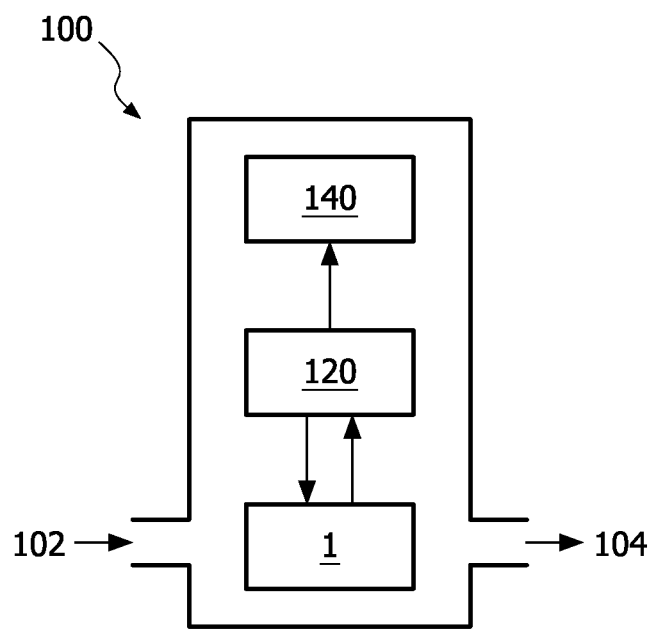
FIG. 9 schematically depicts a NO sensing device in according to an embodiment of the present invention.

FIG. 9 shows an example embodiment of a sensing device 100 comprising a semiconductor device 1 of the present invention. The sensing device 100 is arranged to receive a fluid through inlet 102. The fluid may be air or a body fluid. Preferably, the sensing device 100 is a breath analyzer. The sensing device 100 may further comprise an outlet 104 and a measurement chamber (not shown) in fluidic communication with the inlet 102 and outlet 104. One or more semiconductor devices 1 may be placed in this measurement chamber. The one or more a semiconductor devices 1 are coupled to a signal processor 120 for processing the signal received from the one or more semiconductor devices 1. Said processing includes correlating the signal received from the one or more semiconductor devices 1 to a NO concentration. To this end, the signal processor 120 may for instance comprise a look-up table or an algorithm to make this correlation. Such an algorithm is typically based on the response function of the one or more semiconductor devices 1 to the NO concentration.

The signal processor 120 is arranged to forward the determined NO concentration to an output 140. This may be a display device or a signal output for forwarding the signal to a further device for further processing the output signal, e.g. a computer or an external monitor. An accurate determination of the NO concentration in exhaled breath can be made by using the sensing device 100.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A semiconductor device comprising a pair of electrodes separated from each other to define a channel region in an organic semiconductor layer, a gate structure for controlling said channel region, and a receptor layer at least partially overlapping said channel region, said receptor layer comprising a nitric oxide coordination complex selected from Formula I or Formula II:

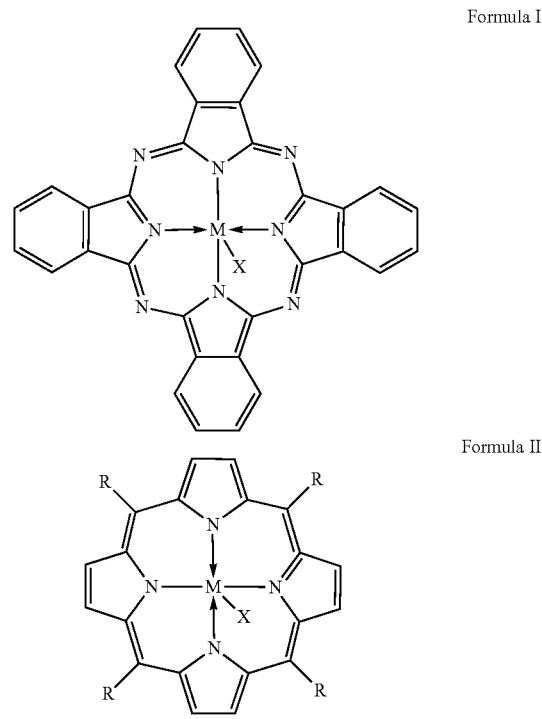

Formula I

Formula II wherein M is Pb or a transition metal ion selected from group 3 to group 12 transition metals, wherein R is an unsubstituted or substituted arylene or heteroarylene functional group and wherein X is a nitride or a halide ion.

2. The semiconductor device of claim 1, wherein the transition metal ion is selected from Sc, Ti, V, Cr, Mn, Fe, Co, Ni, Cu, Pb and Zn.

3. The semiconductor device of claim 2, wherein the transition metal ion is a Fe ion.

4. The semiconductor device of claim 3, wherein the nitric oxide coordination complex is the compound of Formula III:

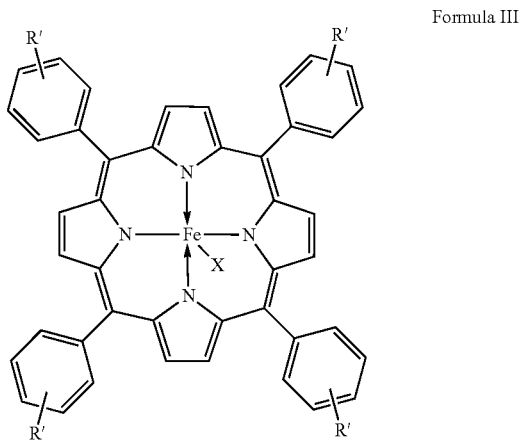

Formula III wherein R' is hydrogen or an alkyl substituent, and wherein X is a halide or nitrate ion.

5. A semiconductor device, comprising:
a pair of electrodes separated from each other to define a channel region in an organic semiconductor layer;
a gate structure for controlling said channel region, and a receptor layer at least partially overlapping said channel region;
wherein the gate structure and the receptor layer are located on opposite sides of the channel region and the receptor layer comprises a nitric oxide coordination complex selected from Formula I or Formula II:

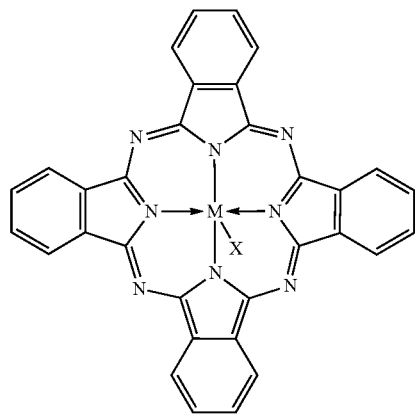

Formula I

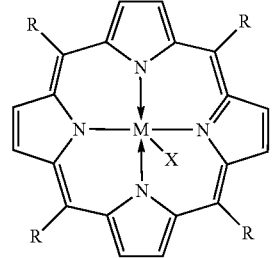

Formula II wherein M is Pb or a transition metal ion selected from group 3 to group 12 transition metals, wherein R is an unsubstituted or substituted arylene or heteroarylene functional group and wherein X is a nitride or a halide ion.

6. The semiconductor device of claim 5, wherein the receptor layer is separated from the channel region by a protective layer.

7. The semiconductor device of claim 1, wherein the receptor layer is arranged over the gate structure.

8. The semiconductor device of claim 1, wherein the organic semiconductor layer covers the electrode pair.

9. The semiconductor device of claim 1, wherein the electrodes are gold electrodes.

10. The semiconductor device of claim 1, wherein the organic semiconductor layer is a self-assembled monolayer, and wherein the nitric oxide coordination complex is spin-coated onto the monolayer.

11. The semiconductor device of claim 1, wherein the receptor layer is separated from the channel region by a protective layer.

12. The semiconductor device of claim 1, wherein the organic semiconductor channel region comprises polyarylamine.

13. A sensing device, comprising:
a measuring chamber in communication with a fluid inlet, said measuring chamber comprising a semiconductor device according to claim 11;
a processor coupled to the semiconductor device for correlating a signal from the semiconductor device to a nitric oxide concentration; and
an output for providing a user with the nitric oxide concentration.

14. The sensing device of claim 13, wherein the sensing device is a breath analyzer.

15. A method of determining a nitric oxide concentration in exhaled breath, said method comprising:
providing a breath analyzer as claimed in claim 14,
exhaling the breath into the inlet; and
determining the NO concentration.

* * * * *